United States Patent [19]

Lindsay

[11] Patent Number: 5,282,783
[45] Date of Patent: Feb. 1, 1994

[54] BLOOD RESERVOIR

[75] Inventor: Erin J. Lindsay, Manchester, Mich.

[73] Assignee: Minnesota Mining and Manufacturing Company, St. Paul, Minn.

[21] Appl. No.: 809,268

[22] Filed: Dec. 17, 1991

[51] Int. Cl.$^5$ .............................................. A61M 1/00
[52] U.S. Cl. ...................................... 604/4; 604/403
[58] Field of Search ................... 604/4, 5, 6, 403, 406, 604/405; 210/321.6, 321.78

[56] References Cited

U.S. PATENT DOCUMENTS

| | | | |
|---|---|---|---|
| 3,891,416 | 6/1975 | Leonard et al. | 55/178 |
| 3,993,461 | 11/1976 | Leonard et al. | 55/178 |
| 4,208,193 | 6/1980 | Munsch et al. | 55/36 |
| 4,243,531 | 1/1981 | Crockett et al. | 210/188 |
| 4,469,659 | 9/1984 | Carson et al. | 422/46 |
| 4,642,089 | 2/1987 | Zupkas et al. | 604/4 |
| 4,656,004 | 4/1987 | Stewart | 422/46 |
| 4,664,682 | 5/1987 | Monzen | 55/178 |
| 4,705,497 | 10/1987 | Shitaokoshi et al. | 604/4 |
| 4,737,139 | 4/1988 | Zupkas et al. | 506/4 |
| 4,818,490 | 4/1989 | Carson et al. | 422/46 |
| 4,846,800 | 7/1989 | Ouriel et al. | 60.4/4 |
| 4,909,780 | 3/1990 | Ouriel et al. | 604/4 |
| 4,923,438 | 5/1990 | Vasconcellos et al. | 604/4 |
| 5,039,430 | 8/1991 | Corey, Jr. | 210/806 |
| 5,127,900 | 7/1992 | Schickling et al. | 604/4 |

FOREIGN PATENT DOCUMENTS

| | | | |
|---|---|---|---|
| 0207304 | 1/1987 | European Pat. Off. | A61M 1/00 |
| 0312101 | 4/1989 | European Pat. Off. | |
| 313107 | 4/1989 | European Pat. Off. | 604/403 |
| 777243 | 2/1935 | France | 604/403 |
| WO9113640 | 9/1991 | PCT Int'l Appl. | |

OTHER PUBLICATIONS

Lindsay Ser. No. 07/493,286 Mar. 14, 1990.
Lindsay Ser. No. 07/686,495 Apr. 17, 1991.
"Sarns Filtered Venous Reservoir" (Catalog No. 9438).
"When you bring efficiency to the surface ... you can lower the prime" (including various brochures).
"Sarns TM SMO/ICR Membrane Oxygenator with Integral Cardiotomy Reservoir: Instuctions".
"Making the Best Even Better" Cobe Laboratories, Inc.
"Cobe CML Ultra: When Priming Volume Really Counts", Cobe Laboratories, Inc.
A. Iatridis, "Laboratory Evaluation of the Variable Prime Cobe Membrane Lung" Proceedings of the American Academy of Cardiovascular Perfusion (Jan. 1985).
"Cobe CML Blood Oxygenator with Integral Filter", Cobe Laboratories, Inc.
"Cobe Membrane Lung (CML) Blood Oxygenator: Performance Characteristics", Cobe Laboratories, Inc.
"Cobe Membrane Lung Ultra 050-122-000 Blood Oxygenator with Integral Filter: Instructions for Use", Cobe Laboratories, Inc.
"Cobe CML: Now Everyone Can Breathe Easier" Cobe Laboratories, Inc.

(List continued on next page.)

*Primary Examiner*—Robert A. Hafer
*Assistant Examiner*—Sam Rimell
*Attorney, Agent, or Firm*—Gary L. Griswold; Walter N. Kirn; Stephen W. Bauer

[57] ABSTRACT

A blood reservoir adapted for use in an extracorporeal circulatory support circuit. The blood reservoir comprises a housing having a chamber for holding blood, an outlet in the housing for draining blood from the chamber, and an inlet for supplying venous blood to the chamber. The inlet includes an inlet tube positioned at a greater elevation in use of the reservoir than the minimum specified level of fluid in the reservoir. A cup-shaped fluid trap is mounted on the inlet tube to trap fluid at the downstream end of the inlet tube. A novel deflector disk is also provided to deflect other fluid from the fluid trap and to mount the fluid trap on the inlet tube.

20 Claims, 3 Drawing Sheets

OTHER PUBLICATIONS

"Cobe VPCML Plus: The Variable Prime Membrane Oxygenator to Meet Your Neonatal, Infant and Pediatric Requirements . . . ", Cobe Laboratories, Inc.

"New Cobe VPCML: One Size Fits Small", Cobe Laboratories, Inc.

E. Iatridis and C. Jenkins, "Equipment Evaluation: Range of Usage of the Variable Prime Cobe Membrane Lung (VPCML)" Persuion 1986.

J. Crockett and P. Grey, "The Variable Prime Cobe Membrane Lung: First Impressions", Perfusion 1987.

"HSVRF Hardshell Venous Reservoir with Integral Cardiotomy Filter: Instructions for Use" Shiley Inc.

"Bard William Harvey H-4700 Series Cardiotomy Reservoir: Directions for Use" C. R. Bard, Inc.

"Gish-ATR TM Blood Recovery/Autotransfusion System: Directions for Use", Gish Biomedical, Inc.

"Hemodynamic Duo" by Gish Biomedical Inc.

"There's Nothing Safer than Your Patient's Own Blood" Gish Biomedical Inc.

"For You, The Gish Cap-35 TM works . . . " Gish Biomedical Inc.

BLOOD RESERVOIR

This invention relates to extracorporeal circulatory support, and more particularly to blood reservoirs used in extracorporeal circulatory support circuits.

BACKGROUND OF THE INVENTION

Extracorporeal support circuits are used to provide circulatory support to patients during cardiovascular surgery. A support circuit of this type includes a venous line for draining blood from the right side of the patient's heart. The venous line delivers the blood to a blood reservoir, such as the venous reservoir sold under the trade designation "SARNS" (Catalog No. 9445) by the Minnesota Mining and Manufacturing Company, St. Paul, Minn. Blood is typically pumped, via a specially designed blood pump, from the outlet of the blood reservoir into a blood oxygenator, such as the oxygenator and heat exchanger sold under the trade designation "SARNS MEMBRANE OXYGENATOR" or "SMO" heat exchanger (Part No. 16310) by the Minnesota Mining and Manufacturing Company, St. Paul, Minn., for oxygenation and cooling. The oxygenated blood is then delivered via an arterial line to the patient. While the pump is running, the patient returns blood to the venous line to repeat the cycle.

The support circuit normally also includes a blood scavenging sub-circuit for recovering blood from the surgical field to recycle the blood. The scavenging sub-circuit includes one or more suckers (typically two to four) for sucking blood from the surgical field. Vacuum is applied to the suckers by a peristaltic positive displacement pump (also known as a roller pump) or wall vacuum to deliver the scavenged blood to a cardiotomy reservoir. A cardiotomy reservoir includes a defoaming section because the scavenged blood normally includes a large amount of entrained air, and a filter for filtering the scavenged blood. The outlet for the cardiotomy reservoir delivers the de-foamed, filtered blood to the venous blood reservoir of the main circuit. U.S. Pat. Nos. 3,891,416; 3,993,461; 4,208,193; and 4,243,531 show various cardiotomy reservoirs.

The cardiotomy reservoir may alternatively be an integral portion of the venous blood reservoir, in which the scavenged blood flows through a filter section and the venous blood does not. Both the scavenged blood and venous blood would flow through a defoaming section. Examples of such combined venous and cardiotomy reservoirs are sold under the following trade designations: "SARNS MEMBRANE OXYGENATOR WITH INTEGRAL CARDIOTOMY RESERVOIR" or "SMO/ICR" (Catalog No. 9462) and "SARNS FILTERED VENOUS RESERVOIR" (Catalog No. 9438) by the Minnesota Mining and Manufacturing Company, St. Paul, Minn.; "HSVRF" hardshell venous reservoir with integral cardiotomy filter by Shiley Inc., Irvine, Calif.; and "BARD WILLIAM HARVEY H-4700 SERIES" cardiotomy reservoir by C. R. Bard, Inc., Billerica, Mass.

Of course, there are numerous permutations of the basic circuit and sub-circuit, in addition to those described above, that have been employed to provide circulatory support.

In extracorporeal support systems of the type described, there has long been interest among other things in (a) minimizing the prime volume of the circuit, (b) minimizing damage (hemolysis) of the blood circulated through the circuit, (c) preventing air emboli being formed in the circuit and delivered to the patient, and (d) preventing loss of prime in the circuit. As a general rule, the lower the prime volume of the circuit, the less donated blood is required. As a result, reducing the prime volume also reduces demand on donated blood supplies, as well as reducing various risks associated with diseases, such as aids and hepatitis B, that can be transmitted by blood notwithstanding careful testing of the blood supply. Reducing hemolysis and preventing air emboli are also widely recognized as beneficial or necessary.

In specifying the minimum fluid volume in venous blood reservoirs, the blood level relative to the outlet of the reservoir has typically been the major consideration. The minimum blood level in such reservoirs has been set high enough relative to the outlet to prevent a vortex being formed by blood exiting the reservoir. A vortex would be undesirable in that with a vortex air might be entrained in the blood exiting the reservoir.

In many venous blood reservoirs, the venous blood inlet is positioned above the minimum blood level, and a defoaming section is provided in the flow path between the inlet and outlet of the reservoir. One reason for the arrangement of the inlet above the minimum blood level is to reduce the time and amount of blood that is in contact with the synthetic material of the defoaming section of the reservoir. When the pump of the main circuit is running, air migration up the inlet is not believed to be a problem. In order to prevent air from migrating up the inlet when the pump is off and to prevent loss of prime in the venous line, it has been the perfusionist's or surgeon's responsibility to clamp the venous line with a suitable clamp (e.g., hemostat) when the pump is turned off to close the venous line to any flow. If both the perfusionist and surgeon fail to clamp the venous line when the pump is turned off, there is a chance that the venous line will lose its prime, with the result that the perfusionist may need to re-prime the venous line before the pump could be restarted.

An integral blood reservoir, heat exchanger and blood oxygenator is available under the trade designation "CML" (Catalog No. 050-104-000) from Cobe Laboratories, Inc., Lakewood, Colo. See, also, U.S. Pat. Nos. 4,818,490 and 4,656,004. That reservoir includes an inlet drop tube extending downwardly into a defoaming element within the reservoir. The lower, downstream end of that drop tube is surrounded in the horizontal direction by an annular flange extending upwardly from a lower surface of the supporting structure for the defoaming element. The annular flange of the "CML" brand reservoir may form a pool of fluid adjacent the downstream end of the drop tube with some fluid trapping action that might help maintain prime in the venous line.

SUMMARY OF THE INVENTION

Generally, a blood reservoir of the invention comprises a housing having top, bottom and side walls defining a chamber for holding blood, an outlet at or adjacent the bottom of the housing for draining fluid (e.g., blood and saline prime solution) from the bottom of the chamber, and an inlet for supplying fluid to the chamber. The inlet and outlet define upstream and downstream directions relative to the normal flow of blood through the reservoir. The inlet includes an inlet tube extending downwardly into the chamber from the top of the chamber and terminating in a downstream end in the chamber. The minimum specified operating level of fluid in the chamber is at a higher elevation than the outlet, but at a lower elevation than the downstream end of the inlet tube. The blood reservoir also includes a generally cup or bowl shaped fluid trap mounted on the inlet tube. The fluid trap has a rim surrounding the inlet tube at an elevation higher than the downstream end of the inlet tube to trap fluid adjacent the downstream end of the inlet tube.

Preferably, the housing is formed of generally rigid, transparent material, and includes indicia of the minimum specified operating level of fluid in the chamber.

Also, preferably, the reservoir further includes a second inlet for supplying blood from a cardiotomy reservoir to the chamber, a funnel in the chamber for directing blood from the second inlet around the outside of the inlet tube, and novel deflector means for deflecting blood from the second inlet away from the fluid trap. The deflector means most preferably comprises a deflector disk mounted on the inlet tube. The deflector disk has a periphery extending outwardly from the inlet tube a greater distance than the rim of the fluid trap.

The fluid trap is most preferably mounted on the inlet tube by the deflector disk with a space formed between the deflector disk and the rim of the fluid trap to allow fluid to exit the fluid trap. The area of the space formed between the deflector disk and the rim of the fluid trap is sufficiently larger than the internal cross sectional area of the inlet tube such that blood exiting the fluid trap in the space formed between the deflector disk and rim of the fluid trap is decelerated relative to blood flowing in the inlet tube. The deflector disk may have a generally annular configuration defining an opening closely receiving the inlet tube, and an upper surface flared generally downwardly from the inlet tube to facilitate blood flow from the second inlet along the upper surface.

Most preferably, the rim of the fluid trap is generally concentric with the inlet tube, and the concave inner surface of the fluid trap faces the lower end of the inlet tube. The diameter of the rim of the fluid trap is sufficiently larger than the diameter of the inlet tube such that blood is decelerated in the fluid trap before exiting the fluid trap over the rim of the fluid trap. For example, the diameter of the rim of the fluid trap is approximately three times the diameter of the inlet tube.

The fluid trap conveniently includes a upwardly-extending convex projection on the concave inner surface of the fluid trap. The convex projection is positioned along a central axis of the inlet tube to facilitate blood flow from the inlet tube along the concave inner surface of the fluid trap.

The blood reservoir is designed to be a component of an extracorporeal circulatory support system comprising, in addition to the reservoir, a venous line for draining blood from a patient, with the inlet of the blood reservoir in fluid communication with the venous line; a blood oxygenator in fluid communication with the outlet of the blood reservoir to oxygenate blood before it is returned to the patient; a pump for pumping blood through the system; and an arterial line for returning oxygenated blood to the patient. Preferably, the pump is positioned relative to blood flow through the system between the outlet of the reservoir and the oxygenator, and the system further includes a heat exchanger associated with the oxygenator for controlling the temperature of the blood being returned to the patient, and a cardiotomy reservoir for filtering and defoaming blood scavenged from the surgical field.

The invention accordingly provides a novel blood reservoir adapted for use in an extracorporeal circulatory support circuit. The blood reservoir is designed to help prevent migration of air through the inlet of the reservoir in the upstream direction, and to help maintain prime in the venous line upstream of the reservoir, particularly in the event that the venous line is not clamped when the pump is turned off. The blood reservoir accomplishes this while allowing the downstream end of its inlet tube to be positioned at a greater elevation than the minimum fluid level in the reservoir.

Because the fluid trap that helps to maintain prime in the venous line is mounted on the inlet tube, other structure, such as the bottom of the reservoir or the bottom of the defoaming element, is not relied upon to provide the fluid trap. Mounting the fluid trap on the inlet tube is believed to facilitate positioning the fluid trap (and the defoaming element) above the normal operating level of fluid in the reservoir. This arrangement also is believed to facilitate assembly of the reservoir with the fluid trap in proper relationship with the inlet tube.

In a second aspect of the invention, the pool of blood or other fluid in the fluid trap is protected from disturbance by other fluid, such as blood from a cardiotomy reservoir, entering the reservoir. This is accomplished by the novel deflector disk, which deflects blood entering the reservoir via a second inlet from the fluid trap, and which mounts the fluid trap on the inlet tube.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF A PREFERRED EMBODIMENT

Figure 1:
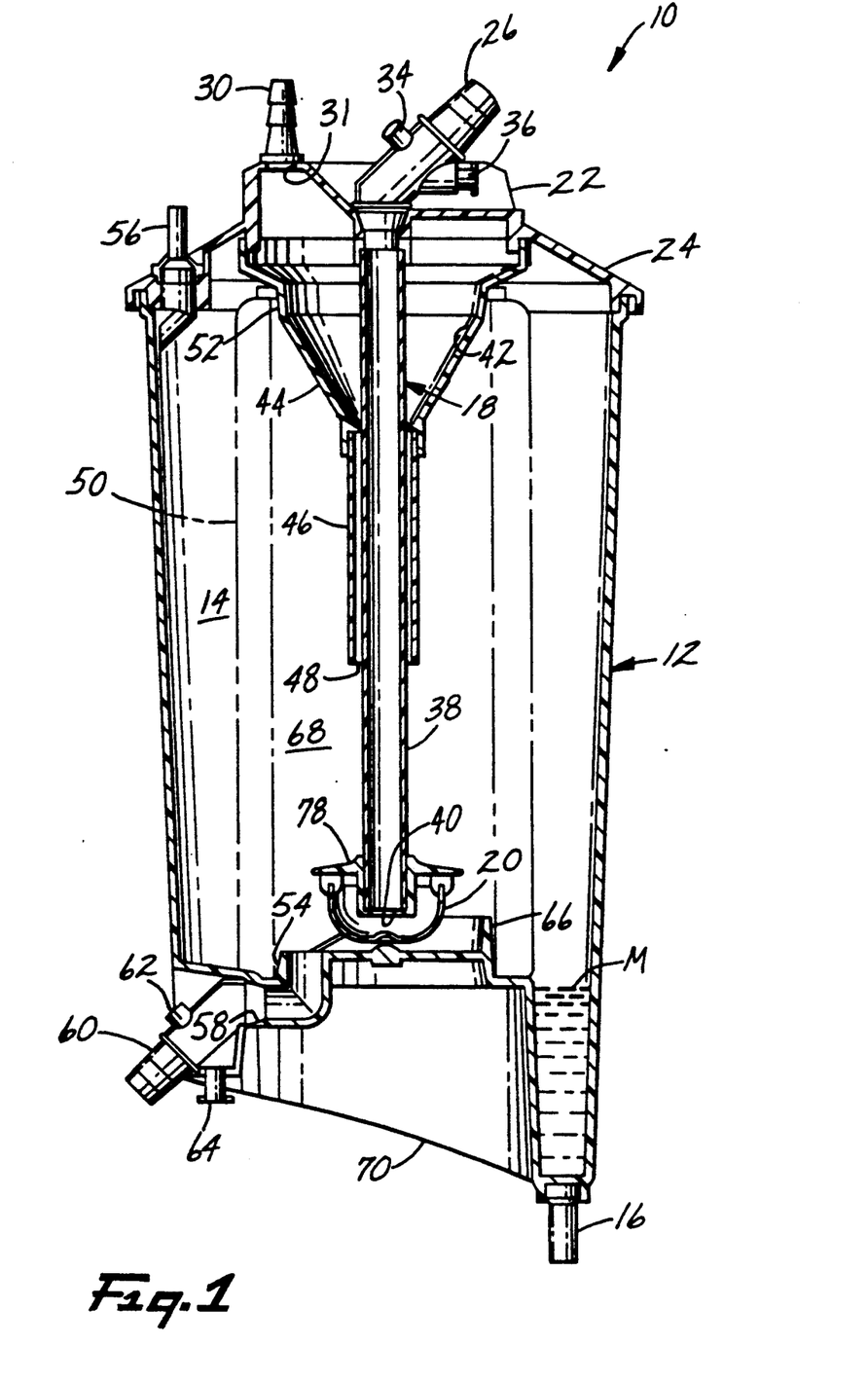
FIG. 1 is a vertical cross-sectional view through a blood reservoir of the invention, showing a novel fluid trap and deflector disk of the invention.

As shown in FIG. 1, a blood reservoir of the invention is designated in its entirety by the reference numeral 10. The blood reservoir 10 generally comprises a housing 12 defining a chamber 14 for holding blood. An outlet 16 is provided in the housing 12 for draining blood from the chamber 14, and an inlet 18 is provided for supplying blood to the chamber 14. The inlet 18 is positioned relative to the outlet 16 such that the inlet 18 is at a greater elevation in use of the reservoir 10 than the outlet 16. The inlet 18 and outlet 16 define upstream and downstream directions relative to the normal flow of blood through the reservoir 10. The blood reservoir 10 includes a novel fluid trap 20 mounted on the inlet 18 for trapping fluid to prevent migration of air in the upstream direction through the inlet 18. As used herein, "fluid trap" refers to structure that collects and holds fluid in a pool at one end of a tube or opening to prevent air from entering that tube or opening through that end.

The housing 12 is formed of generally rigid, transparent material, such as polycarbonate, with indicia provided on the housing 12 at the elevation of the minimum operating fluid level (illustrated by the level of fluid designated at M). The maximum usable volume of the venous reservoir 10 is approximately 4500 ml, and the minimum operating volume is 300 ml.

As illustrated in FIG. 1, a rotatable cap 22 is provided on the top 24 of the housing 12. The rotatable cap 22 includes a tube connection 26 for connecting a venous line (28 in FIG. 4) in fluid communication with the "first" or venous inlet 18 of the reservoir 10, and a tube connection 30 for connecting a line from a cardiotomy reservoir (32 in FIG. 4) in fluid communication with a "second" inlet 31. The venous tube connection 26 includes a luer fitting 34 for receiving a luer hub of a syringe, for example, to inject drugs into the venous inlet, and a fitting 36 for receiving a temperature sensor (not shown) to sense the temperature of the incoming blood. A tube connection (not shown) for receiving prime solution and two additional luer fittings (not shown) are provided on the rotatable cap 22. Typically, the venous tube connection 26 has a ½ inch (13 mm) inside diameter, the cardiotomy tube connection 30 has a ⅜ inch (10 mm) inside diameter, and the prime solution tube connection (not shown) has a ¼ inch (6 mm) inside diameter.

The venous inlet 18 of the reservoir 10 includes an inlet tube 38 extending downwardly from the cap 22 of the reservoir 10 and having a lumen in fluid communication with the lumen formed through the tube connection 28. The inlet tube 38 is preferably about 9.9 inches (250 mm) long to bring the downstream end 40 of the inlet tube 38 to an elevation approximately four inches (100 mm) above the outlet 16 and 1¼ inches (32 mm) above the minimum operating fluid volume. The internal diameter of the inlet tube 38 is approximately ½ inch (13 mm), with an internal cross sectional area of approximately 127 mm².

The second inlet 31 feeds blood from a cardiotomy reservoir 32 into a cavity 42 formed within a funnel 44 concentric with the inlet tube 38. The funnel 44 converges toward the inlet tube 38 in the downward direction to a tube 46 surrounding a portion of the inlet tube 38 and concentric with the inlet tube. The inside diameter of tube 46 is approximately ⅞ inch (22 mm), and the outside diameter of the inlet tube 38 is approximately ⅝ inch (16 mm). The cross sectional area defined between the tube 46 and the inlet tube 38 is approximately 190 mm² (compare to the 71 mm² cross sectional area of the ⅜ inch (10 mm) diameter second inlet 31), and the lower end 48 of tube 46 is approximately 1⅞ inch (48 mm) higher elevation than the downstream end 40 of the inlet tube 38. The arrangement is such that blood from the cardiotomy reservoir 32 enters the cavity 42 through the second inlet 31, flows downwardly along the funnel 44, and then flows downwardly between the tube 46 and the inlet tube 38.

A tubular defoaming element or section designated at 50 is conveniently provided in the chamber 14. The defoaming section 50 extends between a shoulder 52 along the top of the funnel 44 and a shoulder 54 along the bottom of the housing 12. The defoaming section 50 may comprise a central open supporting grid or screen of polypropylene, a open cell foam surrounding the grid, and a sock surrounding the foam. The arrangement is such that blood entering the chamber 14 through the venous inlet 18 or inlet 31 must pass through the defoaming section 50 before it reaches the outlet 16. Most preferably, the bottom of the defoaming section 50 is above the minimum operating fluid level indicated at M.

In one preferred alternative, the defoaming section 50 is positioned completely above the normal operating level of the fluid. By positioning even the lower end of the defoaming section 50 above the normal level of the fluid, contact of blood with the defoaming section 50 is minimized. The defoaming section 50 would then not be partly submerged in a pool of blood unless the level increased by some amount over normal.

The blood reservoir 10 also preferably includes an air vent 56 and additional luer fittings (not shown) on the non-rotatable portion of the top 24. The air vent 56 and additional luer fittings are provided in fluid communication with the portion of the chamber 14 outside the defoaming section 50.

An additional venous inlet 58 may be provided through the bottom of the housing 12. The lower venous inlet 58 is provided to facilitate connecting the venous line 28 to the bottom of the reservoir 10 as an alternative to the upper venous inlet 18 through the top 24 of the reservoir 10. The tube connection 60 of the lower venous inlet 58 is similar to the tube connection 26 of the upper venous inlet 18 in that tube connection 60 includes a luer fitting 62 and a fitting 64 for receiving a temperature sensor to sense the temperature of incoming blood. One advantage of using the lower venous inlet 58 is that blood normally pools in the inlet 58 when the pump (66 in FIG. 4) is turned off because the lower venous inlet 58 is directed upwardly toward the bottom of the chamber 14. One disadvantage of the lower venous inlet 58 is that the temperature sensor and luer fitting 62 are at a more inconvenient position at the bottom of the housing 12.

A generally C-shaped flange 66 is provided on the bottom of the housing 12. The flange 66, which is generally C-shaped when viewed from above, extends upwardly from the floor of the chamber 14 in the cavity 68 formed within the defoaming section 50. The flange 66 is tapered downwardly toward the free ends of the "C" in the direction away from the outlet 16. The bottom of the housing 12 is sloped as illustrated at reference numeral 70 downwardly toward the outlet 16.

The reservoir 10 can be a venous reservoir 10 of the type described above that does not filter scavenged blood from the surgical field 71, or alternatively can be of the combined venous and cardiotomy reservoir type, such as available under the trade designation "SARNS FILTERED VENOUS RESERVOIR" (Catalog No. 9438) from Minnesota Mining and Manufacturing Company, St. Paul, Minn. In this regard, coassigned U.S. patent application Ser. Nos. 07/493,286, filed Mar. 14, 1990, and 07/686,495, filed Apr. 17, 1991, are incorporated herein by reference. The reservoir 10 of this invention most preferably includes the bayonet fastening means (not shown) illustrated in co-assigned U.S. patent application Ser. Nos. 07/493,286 and 07/686,495.

The reservoir 10 may alternatively be of the general types available under the trade designations "SARNS MEMBRANE OXYGENATOR WITH INTEGRAL RESERVOIR" or "SMO/IR" (Catalog No 9461) and "SARNS MEMBRANE OXYGENATOR WITH INTEGRAL CARDIOTOMY RESERVOIR" or "SMO/ICR" (Catalog No. 9462) from Minnesota Mining and Manufacturing Company, St. Paul, Minn. Since other blood reservoirs may also be suitable for application of the invention, the description herein is intended to be illustrative and not limiting.

Figure 2:
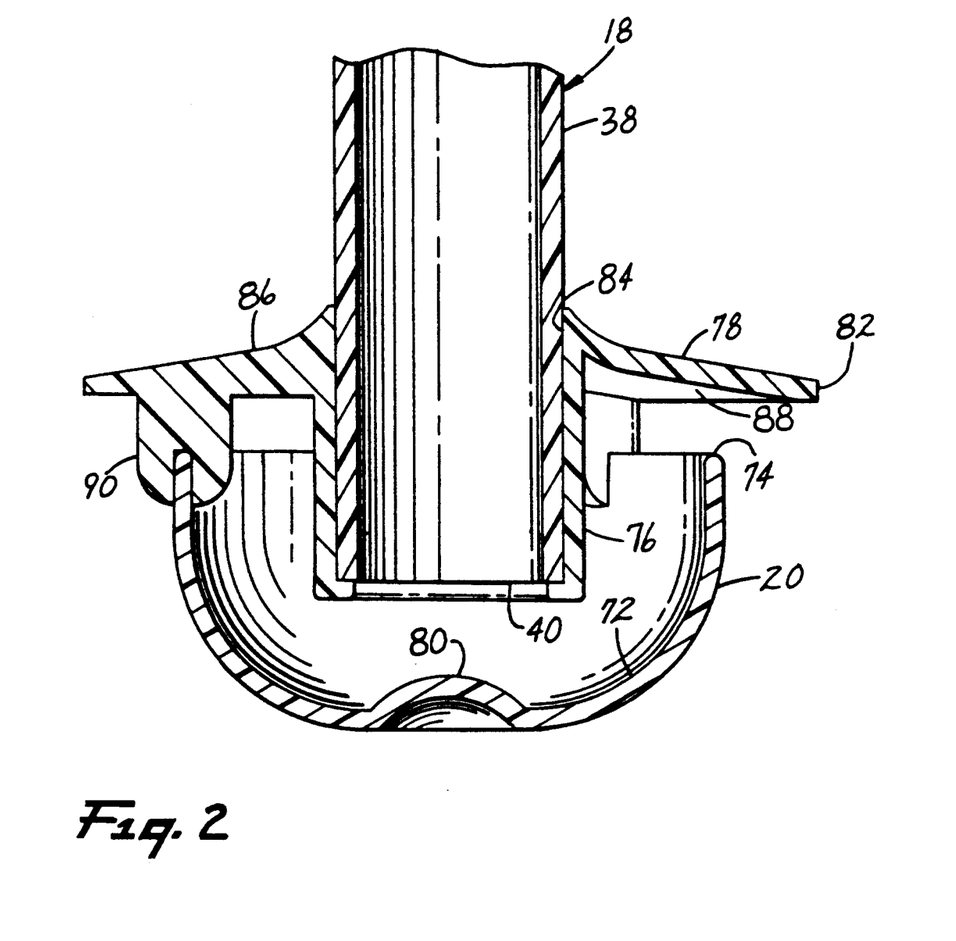
FIG. 2 is an enlarged cross-sectional view of the fluid trap and deflector disk of FIG. 1.
Figure 3:
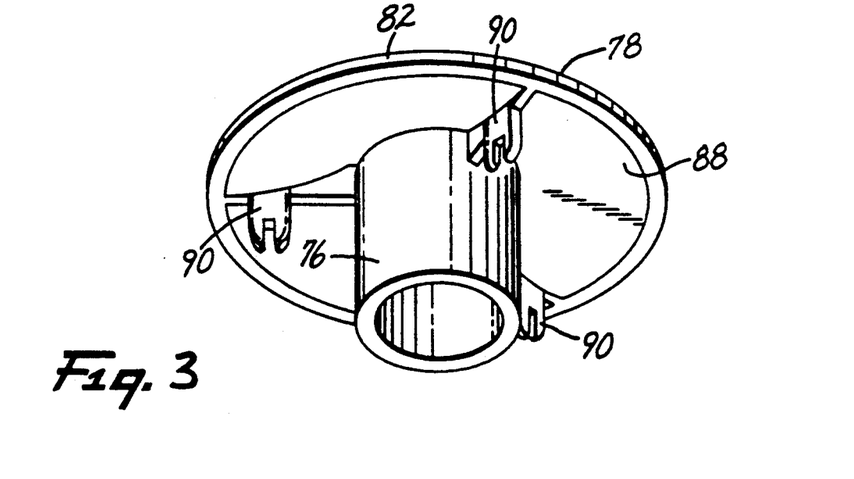
FIG. 3 is an perspective view of the bottom of the deflector disk of FIGS. 1 and 2.

More specifically, as illustrated in FIG. 2, the novel fluid trap 20 preferably comprises a generally bowl or cup shaped fluid trap (also 20) positioned adjacent the lower, downstream end 40 of the inlet tube 38. The fluid trap 20 has a generally concave inner surface 72 facing generally upwardly in use of the reservoir 10 toward the lower end 40 of the inlet tube 38, and a rim 74 with a greater inside diameter than the outside diameter of the inlet tube 38. For example, the rim 74 of the fluid trap 20 may have an inside diameter of approximately 1.4 inches (36 mm) compared to the "effective" outside diameter of the inlet tube 38 of approximately 0.716 inches (18 mm). (As used in this connection, the "effective" outside diameter of the inlet tube 38 includes the cylindrical portion 76 of a novel deflector disk 78 mounted on the inlet tube 38.)

The rim 74 of the fluid trap 20 surrounds the lower, downstream end 40 of the inlet tube 38 at an elevation in use of the reservoir 10 above the lowest elevation (at 40) of the lower end 40 of the inlet tube 38. For example, the rim 74 may be at an elevation approximately 0.35 inches (9 mm) above the lowest elevation of the lower end 40 of the inlet tube 38. This arrangement provides a fluid trap to "trap" some blood or prime solution (e.g., about 10 ml) in the fluid trap 20, thereby preventing migration of air upstream into the inlet tube 38 or venous line 28 and preventing loss of prime in the inlet tube 38 and venous line 28.

The lower end 40 of the inlet tube 38 and the fluid trap 20 are positioned at a greater elevation in use of the reservoir 10 than the indicia M of minimum operating fluid volume. As illustrated in FIG. 1, the bottom of the fluid trap 20 is most preferably spaced upwardly from the floor of the housing 12 so that blood can flow under the fluid trap 20 along the floor of the housing 12.

Most preferably, the rim 74 of the fluid trap 20 is generally circular, and generally concentric with the inlet tube 38. The inside diameter of the rim 74 of the fluid trap 20 is sufficiently larger than the "effective" outside and inside diameter of the inlet tube 38 such that blood is decelerated in the fluid trap 20 before exiting the fluid trap 20 over the rim 74 of the fluid trap 20. For example, the diameter of the rim 74 of the fluid trap 20 is approximately three times the diameter of the inlet tube 38. The arrangement is such that the space formed between the cylindrical portion 76 of the deflector disk 78 and the rim 74 of the fluid trap 20 is substantially larger than the internal cross sectional area of the inlet tube 38. With respect to the illustrative dimensions provided herein, the cross-sectional area defined between the rim 74 and the cylindrical portion 76 is approximately 733 mm$^2$, and the internal cross-sectional area of the inlet tube is approximately 127 mm$^2$. The resulting ratio of these cross sectional areas is approximately 5.8 to one, which is sufficient to cause the blood to decelerate as intended in the fluid trap 20 without reducing the flow rate.

The fluid trap 20 conveniently includes a upwardly-extending convex projection 80 on the concave inner surface 72 of the fluid trap 20. The convex projection 80 is positioned along a central axis of the inlet tube 38 to facilitate blood flow from the inlet tube 38 along the concave inner surface 72 of the fluid trap 20. For example, the convex projection 80 may project approximately 0.075 inches (2 mm) above the inner surface 72 of the fluid trap 20, and the projection 80 may be formed on a radius of curvature of approximately ¼ inch (6 mm) relative to the other illustrative dimensions provided herein.

As illustrated in FIG. 2, the fluid trap 20 may have a somewhat complex configuration including for example a rim 74 having a 1.5 inch (38 mm) outer diameter, and a bottom bending upwardly from adjacent the convex projection 80 toward the rim 74 at a radius of curvature of approximately ½ inches (13 mm). The configuration of the fluid trap 20 is designed to be gentle on the blood being decelerated and re-directed by the inner surface 72.

Preferably, the reservoir 10 further includes novel deflector means (e.g., the deflector disk 78) for deflecting blood from the second inlet 31 away from the fluid trap 20 to prevent that blood from disturbing the blood in the fluid trap 20. As illustrated in FIG. 2, the deflector disk 78 has a cylindrical portion 76 mounted on the inlet tube 38. The periphery 82 of the deflector disk 78 extends outwardly from the cylindrical portion 76 and inlet tube 38 a greater distance than the rim 74 of the fluid trap 20.

The deflector disk 78 may have a generally annular configuration defining an opening 84 closely receiving the inlet tube 38, and an upper surface 86 flared generally downwardly from the inlet tube 38 to facilitate blood flow from the second inlet 31 along the upper surface 86. For example, the deflector disk 78 may have an outer diameter of approximately 2 inches (51 mm) compared to the 1½ inch (38 mm) diameter of the rim 74 of the fluid trap 20, and the upper surface 86 may be sloped downwardly away from the inlet tube 38 at a angle relative to the horizontal of approximately ten degrees.

The fluid trap 20 may conveniently be mounted on the inlet tube 38 by the deflector disk 78 with a space formed between the underside 88 of the deflector disk 78 and the rim 74 of the fluid trap 20 to allow fluid to exit the fluid trap 20. Tabs, such as indicated at 90 in FIG. 2, may be provided projecting from the underside 88 of the deflector disk 78 to mount the fluid trap 20 under the deflector disk 78.

The space formed between the underside 88 of the deflector disk 78 and the rim 74 of the fluid trap 20 is sufficiently larger than the internal cross sectional area of the inlet tube 38 such that blood exiting the fluid trap 20 in the space formed between the deflector disk 78 and rim 74 of the fluid trap 20 is decelerated relative to blood flowing in the inlet tube 38. For example, the annular open area defined as projecting upwardly from the rim 74 of the fluid trap 20 to the underside 88 of the deflector disk 78 may be approximately 588 mm$^2$ in comparison with the internal cross sectional area of the inlet tube 38 being 127 mm$^2$, which corresponds approximately to a 4.6 to one ratio between the areas the blood must flow through between the rim 74 and underside 8 of the deflector disk 78, on the one hand, and in the inlet tube 38, on the other hand.

Figure 4:
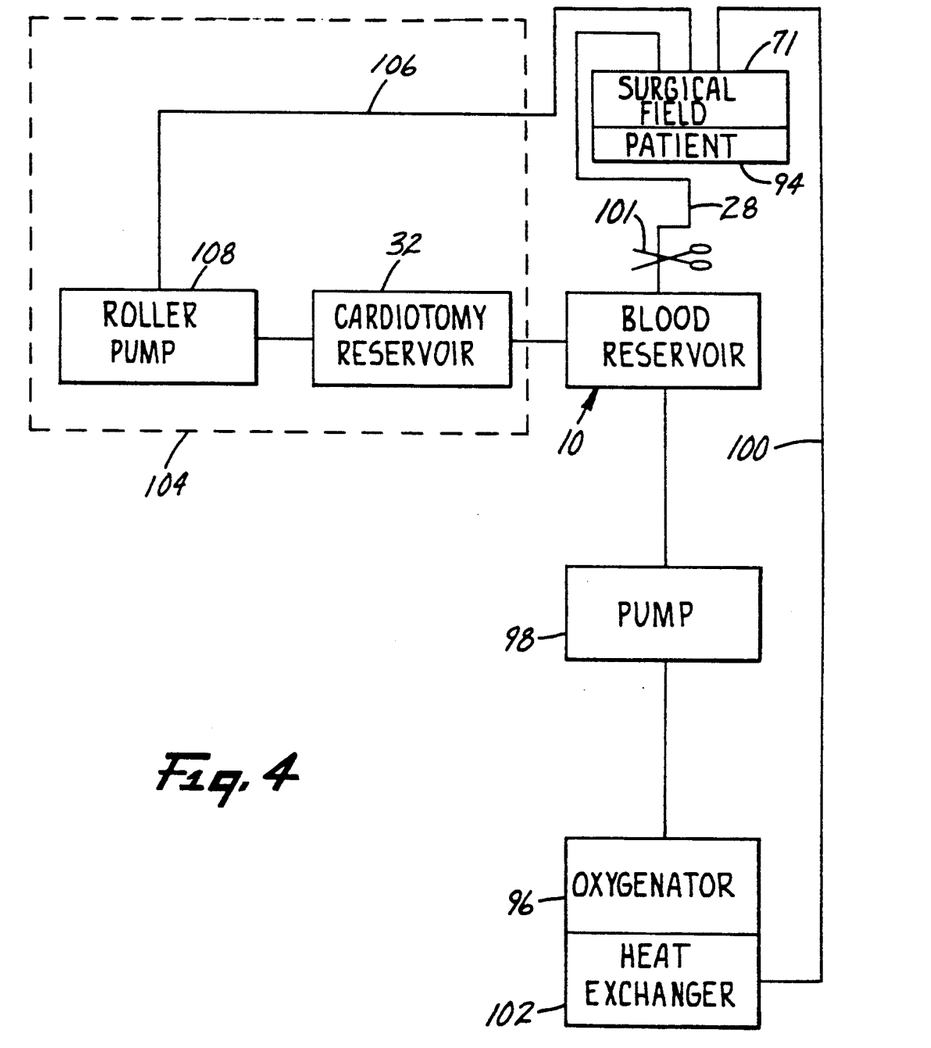
FIG. 4 is a schematic diagram of an extracorporeal circulatory support circuit including the blood reservoir of FIGS. 1-3.

As illustrated in FIG. 4, the blood reservoir 10 is designed to be a component of an extracorporeal circulatory support system 92. System 92 includes, in addition to the reservoir 10, a venous line 28 for draining blood from a patient 94, with the venous inlet 18 of the blood reservoir 10 in fluid communication with the venous line 28; a blood oxygenator 96 in fluid communication with the outlet 16 of the blood reservoir 10 to oxygenate blood before it is returned to the patient 94; a pump 98 for pumping blood and prime solution through the system 92; and an arterial line 100 for returning oxygenated blood to the patient 94. A clamp or hemostat 101 is normally provided to clamp the venous line 28.

Preferably, the pump 98 is positioned relative to blood flow through the system 92 between the outlet 16 of the blood reservoir 10 and the inlet of the oxygenator 86, although other arrangements may be employed. The pump 98 may be of any suitable type, including a conventional roller pump (also known as peristaltic or positive displacement pumps), and a centrifugal pump. Suitable roller pumps have been available as part of the system available under the trade designation "SARNS 9000" from Minnesota Mining and Manufacturing Company, St. Paul, Minn., and suitable centrifugal pumps are shown in co-assigned U.S. Pat. Nos. 4,589,822; 4,606,698; 4,690,002; 4,778,445; 4,781,525 and 4,984,972 (incorporated herein by reference), and have been available under the trade designation "SARNS 7850 Centrifugal Pump" from Minnesota Mining and Manufacturing Company, St. Paul, Minn.

A suitable blood oxygenator 96 has been available under the trade designation "SARNS Membrane Oxygenator" or "SMO" from Minnesota Mining and Manufacturing Company, St. Paul, Minn. U.S. Pat. Nos. 3,794,468; 3,927,980; and 4,690,758 show various features of blood oxygenators, and are incorporated herein by reference. The "SARNS" brand oxygenator 96 includes a heat exchanger 102 mounted on the oxygenator 96 for controlling the temperature of the blood being returned to the patient 94.

As illustrated at 104 in FIG. 4, the system 92 would normally include a blood scavenging sub-circuit (also 104). The blood scavenging sub-circuit includes one or more conventional blood suckers 106 for sucking blood from the surgical field 71, a roller pump 108 (or other suitable source of vacuum) for applying vacuum to the blood suckers 106, and the cardiotomy reservoir 32 for filtering and defoaming blood scavenged from the surgical field 71. The outlet of the cardiotomy reservoir 32 is in fluid communication with inlet 31 of the venous reservoir 10 to supply the filtered blood to the venous reservoir 10. Cardiotomy reservoirs are shown in U.S. Pat. Nos. 3,891,416; 3,993,461; 4,208,193 and 4,243,531, which are incorporated herein by reference.

OPERATION

The components of the support system 92 are first connected together as is well known in the art. The patient ends of the arterial line 100 and venous line 28 are connected together, and saline prime solution is added to the blood reservoir 10 through a prime inlet (not shown). The pump 98 is activated to pump the saline prime solution through the various lines 100, 28, oxygenator 96, and heat exchanger 102 to eliminate air from those components. (The system 92 should be closed to air except in the blood reservoir.) Other aspects of the operation of such systems 92, such as the operation of the scavenging sub-circuit and cardioplegia administration, will not be discussed herein.

The blood reservoir 10 is placed at a lower elevation than the patient 94, with the venous line 28 and arterial line 100 draped from the patient 94. Portions of the venous line 28 may be at a higher elevation than both the patient 94 and the blood reservoir 10.

The system 92 is now ready to be connected to the patient 94 to perfuse the saline and blood into the patient 94 in conventional fashion. At some point, the perfusionist will shut the pump 98 down to stop perfusion. The normal practice in many systems of this general type is to clamp the venous line with the hemostat 101 to prevent de-priming of the venous line and inlet tube and migration of air up the inlet tube and venous line. If that practice is not followed and the venous line 28 is not clamped, the fluid trap 20 of the invention will prevent migration of air up the inlet tube 38 and venous line 28 and de-priming of the inlet tube 38 and venous line 28 while the pump 98 is not running.

As various changes could be made in the above constructions without departing from the scope of the invention, it is intended that all matter contained in the above description or shown in the accompanying drawing be interpreted as illustrative and not in a limiting sense.

I claim:

1. A blood reservoir adapted for use in an extracorporeal circulatory support circuit, the blood reservoir comprising:
   a housing having top, bottom and side walls defining a chamber inside the housing for holding fluid;
   an outlet adjacent the bottom of the housing for draining fluid from the bottom of the chamber, the chamber of the housing having a minimum specified operating level of fluid therein at an elevation greater than the outlet;
   an inlet for supplying fluid to the chamber, the inlet and outlet defining upstream and downstream directions relative to the normal flow of blood through the reservoir, the inlet including an inlet tube extending generally downwardly into the chamber from the top of the housing and terminating at a downstream end, the downstream end of the inlet tube being positioned at a greater elevation in use of the reservoir than the minimum specified operating level of fluid, the inlet including a tube connection on the top of the housing for connecting tubing in fluid communication with the inlet; and
   a bowl shaped fluid trap in the chamber and mounted on the inlet tube, the fluid trap having a rim surrounding the inlet tube at an elevation higher than the downstream end of the inlet tube to trap fluid adjacent the downstream end of the inlet tube.

2. A blood reservoir according to claim 1 wherein the housing is transparent, and includes indicia of the minimum specified operating level of fluid in the chamber.

3. A blood reservoir according to claim 2 wherein the inlet tube extends into the chamber from the top of the housing, the fluid trap having a generally concave inner surface facing generally upwardly in use of the reservoir toward the downstream end of the inlet tube, the blood reservoir further including a defoaming element in the chamber through which fluid must flow to reach the outlet from the inlet, the defoaming element having a lower end positioned at an elevation higher than the indicia of the minimum specified operating level of fluid in the chamber.

4. A blood reservoir according to claim 3 wherein the chamber of the housing defines a normal operating level of fluid in the chamber at an elevation greater than the minimum specified operating level of fluid, the lower end of the defoaming element being spaced above the bottom of the chamber at an elevation higher than the normal operating level of fluid in the chamber.

5. A blood reservoir according to claim 3 wherein the inlet constitutes a first inlet for supplying venous blood to the chamber, the reservoir further including:
- a second inlet for supplying blood from a cardiotomy reservoir to the chamber; and
- a deflector disk mounted on the inlet tube for deflecting blood from the second inlet away from the fluid trap, the deflector disk having a periphery extending outwardly from the inlet tube a greater distance than the rim of the fluid trap.

6. A blood reservoir according to claim 5 wherein the fluid trap is mounted on the inlet tube by the deflector disk with a space formed between the deflector disk and the rim of the fluid trap to allow fluid to exit the fluid trap.

7. A blood reservoir according to claim 6 further comprising a funnel in the housing for directing blood from the second inlet around the outside of the inlet tube; the deflector disk having a generally annular configuration defining an opening closely receiving the inlet tube, the deflector disk having an upper surface flared generally downwardly from the inlet tube to facilitate blood flow from the second inlet along the upper surface, the space formed between the deflector disk and the rim of the fluid trap being greater than the internal cross sectional area of the inlet tube such that blood exiting the fluid trap between the deflector disk and the rim of the fluid trap is decelerated relative to blood flowing in the inlet tube.

8. A blood reservoir according to claim 5 wherein the inlet tube is generally cylindrical, and rim of the fluid trap is generally circular and generally concentric with the inlet tube, the concave inner surface of the fluid trap facing the downstream end of the inlet tube, the fluid trap including a upwardly-extending convex projection on the concave inner surface of the fluid trap, the convex projection being positioned along a central axis of the inlet tube to facilitate blood flow from the inlet tube along the concave inner surface of the fluid trap.

9. A blood reservoir according to claim 8 wherein the diameter of the rim of the fluid trap is sufficiently larger than the diameter of the inlet tube such that the cross sectional area defied between the rim of the fluid trap and the inlet tube is greater than the internal cross sectional area of the inlet tube so that blood is decelerated in the fluid trap before exiting the fluid trap over the rim of the fluid trap.

10. An extracorporeal circulatory support system for supporting a patient during cardiovascular surgery, the system comprising:
- a venous line for draining blood from a patient;
- a blood reservoir comprising a housing having top, bottom and side walls defining a chamber inside the housing for holding fluid; an outlet at or adjacent the bottom of the housing for draining fluid from the bottom of the chamber; the chamber of the housing having a minimum specified operating level of fluid therein at an elevation greater than the outlet; and inlet in fluid communication with the venous line for supplying fluid to the chamber, the inlet and outlet defining upstream and downstream directions relative to the normal flow of blood through the reservoir, the inlet including an inlet tube extending generally downwardly into the chamber from the top of the housing and terminating in a downstream end in the chamber, the downstream end of the inlet tube being positioned at a greater elevation in use of the reservoir than the minimum specified operating level of fluid, the inlet including a tube connection on the top of the housing for connecting the venous line in fluid communication with the inlet tube; and a bowl shaped fluid trap in the chamber and mounted on the inlet tube, the fluid trap having a rim surrounding the inlet tube at an elevation higher than the downstream end of the inlet tube to trap fluid adjacent the downstream end of the inlet tube;
- a blood oxygenator in fluid communication with the outlet of the blood reservoir to oxygenate blood before it is returned to the patient;
- a pump for pumping blood through the system; and
- an arterial line for returning oxygenated blood to the patient.

11. A system according to claim 10 wherein the pump is positioned relative to blood flow through the system downstream of the outlet of the reservoir between the outlet of the reservoir and the patient.

12. A system according to claim 11 wherein the pump is positioned relative to blood flow through the system between the outlet of the reservoir and the oxygenator, the system further including a heat exchanger associated with the oxygenator for controlling the temperature of the blood being returned to the patient.

13. A system according to claim 10 wherein the housing of the blood reservoir is generally transparent, and includes indicia of the minimum specified operating level of fluid in the chamber.

14. A system according to claim 13 wherein the fluid trap has a generally concave inner surface facing generally upwardly in use of the reservoir toward the downstream end of the inlet tube; the blood reservoir further including a defoaming element in the chamber through which fluid must flow to reach the outlet from the inlet, the defoaming element having a lower end positioned at a greater elevation than the indicia of the minimum specified operating level of fluid in the reservoir.

15. A system according to claim 14 wherein the chamber of the housing defines a normal operating level of fluid in the chamber at an elevation greater than the minimum specified operating level of fluid, the lower end of the defoaming element being spaced above the bottom of the chamber at an elevation higher than the normal operating level of fluid in the chamber.

16. A system reservoir according to claim 14 further comprising a cardiotomy reservoir for filtering blood scavenged from the surgical field, the inlet of the blood reservoir constituting a first inlet for supplying venous blood to the chamber, the blood reservoir further including:
- a second inlet in fluid communication with the cardiotomy reservoir for supplying blood from a cardiotomy reservoir to the chamber; and
- deflector disk mounted on the inlet tube for deflecting blood from the second inlet away from the fluid trap, the deflector disk having a periphery extending outwardly from the inlet tube a greater distance than the rim of the fluid trap.

17. A system according to claim 16 wherein the fluid trap is mounted on the inlet tube by the deflector disk with a space formed between the deflector disk and the rim of the fluid trap to allow fluid to exit the fluid trap, the space formed between the deflector disk and the rim of the fluid trap being greater than the internal cross sectional area of the inlet tube such that blood exiting the fluid trap between the deflector disk and the rim of the fluid trap is decelerated relative to blood flowing through the inlet tube.

18. A system according to claim 17, wherein the deflector disk of the blood reservoir has a generally annular configuration defining an opening closely receiving the inlet tube, the deflector disk having an upper surface flared generally downwardly from the inlet tube to facilitate blood flow from the second inlet along the upper surface; the blood reservoir further comprising a funnel in the chamber for directing blood from the second inlet around the outside of the inlet tube.

19. A system according to claim 14 wherein the inlet tube is generally cylindrical, and the rim of the fluid trap is generally circular and concentric with the inlet tube, the concave inner surface of the fluid trap facing the lower end of the inlet tube, the fluid trap further including an upwardly-extending convex projection on the concave inner surface of the fluid trap, the convex projection being positioned along a central axis of the inlet tube to facilitate blood flow from the inlet tube along the concave inner surface of the fluid trap.

20. A system according to claim 19 wherein the housing of the blood reservoir is formed of generally rigid material.

* * * * *

UNITED STATES PATENT AND TRADEMARK OFFICE
CERTIFICATE OF CORRECTION

PATENT NO. : 5,282,783
DATED : February 1, 1994
INVENTOR(S) : Erin J. Lindsay

It is certified that error appears in the above-indentified patent and that said Letters Patent is hereby corrected as shown below:

Col. 5, line 25, "5/8" should read --3/8--.

Col. 8, line 57, "8" should read --88--.

Col. 11, line 43, "defied" should read --defined--.

Signed and Sealed this

Twenty-eight Day of February, 1995

Attest:

BRUCE LEHMAN

Attesting Officer

Commissioner of Patents and Trademarks